US012746189B2

(12) United States Patent
Jin et al.

(10) Patent No.: US 12,746,189 B2
(45) **Date of Patent: *Sep. 29, 2026**

(54) ANTIPERSPIRANT EMULSION

(71) Applicant: Conopco, Inc., Englewood Cliffs, NJ (US)

(72) Inventors: Huajin Jin, Shanghai (CN); Xiaoke Li, Shanghai (CN)

(73) Assignee: Conopco Inc., Hoboken, NJ (US)

( * ) Notice: Subject to any disclaimer, the term of this patent is extended or adjusted under 35 U.S.C. 154(b) by 639 days.

This patent is subject to a terminal disclaimer.

(21) Appl. No.: 17/762,432

(22) PCT Filed: Oct. 8, 2020

(86) PCT No.: PCT/EP2020/078191
§ 371 (c)(1),
(2) Date: Mar. 22, 2022

(87) PCT Pub. No.: WO2021/073988
PCT Pub. Date: Apr. 22, 2021

(65) Prior Publication Data

US 2022/0347065 A1 Nov. 3, 2022

(30) Foreign Application Priority Data

Oct. 16, 2019 (WO) ................ PCT/CN2019/111460
Nov. 14, 2019 (EP) .................................... 19209021

(51) Int. Cl.

| | |
|---|---|
| ***A61K 8/06*** | (2006.01) |
| ***A61K 8/34*** | (2006.01) |
| ***A61K 8/365*** | (2006.01) |
| ***A61K 8/92*** | (2006.01) |
| ***A61Q 15/00*** | (2006.01) |
| ***A61Q 17/00*** | (2006.01) |

(52) U.S. Cl.
CPC .............. *A61K 8/062* (2013.01); *A61K 8/342* (2013.01); *A61K 8/365* (2013.01); *A61K 8/922* (2013.01); *A61Q 15/00* (2013.01); *A61Q 17/005* (2013.01); *A61K 2800/21* (2013.01); *A61K 2800/30* (2013.01); *A61K 2800/874* (2013.01)

(58) Field of Classification Search
None
See application file for complete search history.

(56) References Cited

U.S. PATENT DOCUMENTS

| | | | | |
|---|---|---|---|---|
| 4,814,165 | A * | 3/1989 | Berg | A61K 8/0229 424/59 |
| 6,503,944 | B1 | 1/2003 | Chanchani | |
| 2004/0120909 | A1 | 6/2004 | Lee et al. | |
| 2019/0060184 | A1 * | 2/2019 | Doering | A61K 8/062 |
| 2019/0105240 | A1 * | 4/2019 | Oelrichs | A61K 8/062 |
| 2022/0401347 | A1 | 12/2022 | Jin et al. | |

FOREIGN PATENT DOCUMENTS

| | | |
|---|---|---|
| CN | 1365271 | 8/2002 |
| CN | 103974686 | 8/2014 |
| DE | 102014221802 | 4/2016 |
| DE | 102016000191 | 1/2017 |
| DE | 102016208863 | 3/2017 |
| EP | 0545556 | 6/1993 |
| EP | 1473016 | 11/2004 |
| EP | 2008638 | 12/2008 |
| EP | 2191818 | 6/2010 |
| EP | 2604248 | 6/2013 |
| RU | 2333741 | 9/2008 |
| RU | 2567054 | 10/2015 |
| WO | WO9515812 | 6/1995 |
| WO | WO0074640 | 12/2000 |
| WO | WO0152805 | 7/2001 |
| WO | WO2006018073 | 2/2006 |
| WO | WO2009007089 | 1/2009 |
| WO | WO2010003828 | 1/2010 |
| WO | WO2010003862 | 1/2010 |
| WO | WO2010145909 | 12/2010 |
| WO | WO2011040911 | 4/2011 |
| WO | WO2013087516 | 6/2013 |
| WO | WO2017190775 | 11/2017 |
| WO | WO2018010906 | 1/2018 |
| WO | WO2018099931 | 6/2018 |
| WO | WO2018111664 | 6/2018 |
| WO | WO2018111704 | 6/2018 |

(Continued)

OTHER PUBLICATIONS

Sorbeth-20 Beeswax, Cosmetics Info, available at https://www.cosmeticsinfo.org/ingredient/sorbeth-20-beeswax/, accessed on Jan. 22, 2025 (Year: 2025).*
Database GNPD (Online) Mintel; Ice Pure Oxygen 24h Doedorant; Williams Expert; Oct. 21, 2013; pp. 1-3, XP055581649, Record ID 2212470; Spain.
Search Report and Written Opinion in EP19209017; May 14, 2020; European Patent Office (EPO).
Search Report and Written Opinion in EP19209021; Mar. 18, 2020; European Patent Office (EPO).
Database GNPD (Online) Mintel; Natural Deodorant; Primal Pit Paste Lavender; Oct. 19, 2017; pp. 1-3, XP055689707, Record ID 5167881; United States of America.
Database GNPD (Online) Mintel; Lavender Deodorant; The Ohm Collection; Sep. 25, 2017; pp. 1-2, XP055689713, Record ID 5127677; France.

(Continued)

*Primary Examiner* — H. Sarah Park
(74) *Attorney, Agent, or Firm* — Stephanie Huang

(57) ABSTRACT

The present invention is in the field of antiperspirant compositions, in particular, compositions comprising antiperspirant actives. Disclosed is an antiperspirant composition free from aluminum and/or zirconium salt, and/or zinc based antiperspirant active, comprising an oil-in-water emulsion comprises oil phase and an emulsifier, wherein said oil phase comprises a lipophilic material having a melting point greater than 40° C.; wherein said composition comprises at least 4 wt % of said lipophilic material.

6 Claims, No Drawings

(56) References Cited

FOREIGN PATENT DOCUMENTS

| | | |
|---|---|---|
| WO | WO2018111706 | 6/2018 |
| WO | WO2019192695 | 10/2019 |

OTHER PUBLICATIONS

Database GNPD (Online) Mintel; Natural Deodorant; Primal Pit Paste Lavender; Apr. 4, 2017; pp. 1-4, XP055689729, Record ID 4721419; United States of America.
Search Report and Written Opinion in PCTEP2020078191; Dec. 14, 2020; World Intellectual Property Org. (WIPO).
Search Report and Written Opinion in PCTEP2020078192; Oct. 28, 2020; World Intellectual Property Org. (WIPO).
IPRP2 in PCTEP2020078191; Sep. 29, 2021; World Intellectual Property Org. (WIPO).
IPRP2 in PCTEP2020078192; Feb. 25, 2022; World Intellectual Property Org. (WIPO).
Written Opinion 2 in PCTEP2020078192; Oct. 8, 2021; World Intellectual Property Org. (WIPO).
Database GNPD (Online) Mintel; Relaxing Deodorant Roll-On; Love Beauty and Planet; Mar. 2019; pp. 1-2, Record ID 6415027; Belgium.
Database GNPD (Online) Mintel; Cool Ocean Deodorant Roll-On; Zuo Yan You Se for Men; Aug. 2018; pp. 1-2, Record ID 5897607; China.
Database GNPD (Online) Mintel; Talc Deodorant; SMA; Oct. 2008; pp. 1-2, Record ID 984163; Italy.
Database GNPD (Online) Mintel; Moisturizing Deodorant Cream; Amazongreen Açaí com Ervas; Nov. 2016; pp. 1-2, Record ID 4407679; Brazil.
Database GNPD (Online) Mintel; Deodorant Cream; Apiarium Propoli; Jul. 2014; pp. 1-2, Record ID 2544919; Italy.
Database GNPD (Online) Mintel; Deodorant Cream; Sauber Deo 7; Sep. 2011; pp. 1-2, Record ID 1627534; Italy.
Database GNPD (Online) Mintel; 72h Deodorant Cream; Sauber Deoactive; Oct. 2017; pp. 1-2, Record ID 5168671; Italy.
Database GNPD (Online) Mintel; 7 Days Deodorant Cream; Sauber Deocare; Mar. 2017; pp. 1-2, Record ID 4705081; Italy.
Database GNPD (Online) Mintel; Roll-On Deodorant for Children; Bob Esponja; Feb. 2012; pp. 1-2, Record ID 1718734; Mexico.
Database GNPD (Online) Mintel; Deodorant; Clean Warm Cotton; Sep. 2011; pp. 1-2, Record ID 1606636; United States of America.
Database GNPD (Online) Mintel; Moisture-Absorbent Deodorant; Clean Original; Jul. 2011; pp. 1- 2, Record ID 1586364; United States of America.
Database GNPD (Online) Mintel; 7 Days Deodorant Cream; Sauber; May 2011; pp. 1-2, Record ID 1552439; Italy.
Database GNPD (Online) Mintel; Mediterranean Citrus Deodorant Spray; I Frari Agrumi; Jun. 2010; pp. 1-2, Record ID 1341998; Italy.
Database GNPD (Online) Mintel; Antiodorant Cream; Claro; Sep. 2006; pp. 11, Record ID590982; Saudi Arabia.
Database GNPD (Online) Mintel; 7 Days Hypoallergenic Deodorant Cream; Sauber; Jul. 2005; pp. 1-2, Record ID 377105; Italy.
Database GNPD (Online) Mintel; Deodorant Stick Reformulation; Natural Honey; Jun. 2005; pp. 1-2, Record ID 10222679; Argentina.
Database GNPD (Online) Mintel; Deodorant Spray; Clinians; Nov. 2004; pp. 1-2, Record ID 313687; Italy.
Database GNPD (Online) Mintel; Natural Honey Deo Stick; Revlon; Sep. 2003; pp. 1-1, Record ID 229570; Denmark.
Database GNPD (Online) Mintel; Deodorant Stick; Johnson & Johnson; Feb. 1999; pp. 1-1, Record ID 2621; Italy.
Database GNPD (Online) Mintel; Deodorant; For Pits Sake !; Sep. 2012; pp. 1-3, Record ID 1855386, XP055689580; United States of America.

* cited by examiner

ANTIPERSPIRANT EMULSION

CROSS REFERENCE TO RELATED APPLICATIONS

The present application is a U.S. National Phase Application under 35 U.S.C. § 371 of International Application No. PCT/EP2020/078191, filed on Oct. 8, 2020, which claims priority to International Application No. PCT/CN2019/111460, filed on Oct. 16, 2019, and European Patent Application No. 19209021.5, filed on Nov. 14, 2019, the contents of which are incorporated herein in their entireties.

FIELD OF THE INVENTION

The present invention is in the field of antiperspirant compositions.

BACKGROUND OF THE INVENTION

The present invention relates to compositions that contain antiperspirant actives. These actives are added to compositions to reduce perspiration upon topical application of the compositions to the body, particularly to the underarm regions of the human body viz. the axilla, and sometimes even on the upper part of the body near the chest.

Usually, conventional antiperspirant actives are salts of certain metals having an astringent effect, such as the salts of aluminium and/or zirconium. Since antiperspirants are used regularly, and have been used for decades, there is an ever-increasing need to develop alternative antiperspirant actives which are equally efficacious.

WO 18111706 A1 (Colgate Palmolive, 2017) discloses an antiperspirant/deodorant composition comprising an oil-in-water emulsion base and an antiperspirant active dispersed in an aqueous phase of the oil-in-water emulsion base. Such antiperspirant &/or deodorant compositions disclosed may include a plant-based oil having a melting point of −15 to 38° C.

WO 18111704 A1 (Colgate Palmolive, 2017) discloses an antiperspirant/deodorant composition comprising: an oil-in-water emulsion base comprising: an emulsifier comprising a mixture of steareth-2 and steareth-20, a plant-based oil, a polyol, water; and an antiperspirant active dispersed in the oil-in-water emulsion base, wherein the antiperspirant active consists essentially of a zinc-based antiperspirant active.

WO 10145909 A1 (Unilever, 2010) discloses use of a lamellar phase stabilized oil-in-water emulsion as an antiperspirant agent or sweat reducing agent. The oil of the oleosome dispersions should preferably remain in a liquid state at temperatures as low as 20° C. or even 15° C.

EP 2604248 B1 (Unilever, 2011) discloses oil-in-water emulsion cosmetic compositions and methods of making the same. It particularly relates to aqueous antiperspirant compositions suitable for roll-on application and to aqueous cosmetic compositions comprising 12-hydroxystearic acid.

SUMMARY OF THE INVENTION

The present inventors have surprisingly observed that oil-in-water emulsion droplet comprising lipophilic materials can lead to a reduction in perspiration. Once the oil-in-water emulsion droplet has been applied on skin and once the water of the emulsion has evaporated to some extent at least, the emulsion droplet is broken down and lipophilic materials which are in solid form, that were earlier emulsified in the medium, are now free to coalesce or bond with each other and form an aggregation/precipitation. The aggregation/precipitation that is formed is then capable of preventing sweat from rapidly being released. In this manner, the lipophilic materials which are in solid form behave much like conventional antiperspirants. The lipophilic materials of the present invention should be in solid form when being applied which distinguishes them from other lipophilic materials which become liquid when they are applied.

In accordance with a first aspect is disclosed an antiperspirant composition free from aluminum and/or zirconium salt, and/or zinc based antiperspirant active, comprising an oil-in-water emulsion comprises oil phase and a surfactant, wherein said oil phase comprises a lipophilic material having a melting point greater than 40° C.; wherein said composition comprises at least 4 wt % of said lipophilic material.

In accordance with a second aspect is disclosed a method of reducing perspiration comprising a step of topical application of the composition of the first aspect on to the desired skin surface.

In accordance with a third aspect is disclosed use of the composition of the first aspect for reduction of bodily perspiration.

All other aspects of the present invention will more readily become apparent upon considering the detailed description and examples which follow.

Except in the examples, or where otherwise explicitly indicated, all numbers in this description indicating amounts of material or conditions of reaction, physical properties of materials and/or use may optionally be understood as modified by the word “about”.

All amounts are by weight of the antiperspirant composition, unless otherwise specified.

It should be noted that in specifying any ranges of values, any particular upper value can be associated with any particular lower value.

For the avoidance of doubt, the word “comprising” is intended to mean “including” but not necessarily “consisting of” or “composed of”. In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

DETAILED DESCRIPTION OF THE INVENTION

By “An antiperspirant Composition” as used herein, is meant to include a composition for topical application to the skin of mammals, especially humans. Such a composition is preferably of the leave-on type. By a leave-on composition is meant a composition that is applied to the desired skin surface and left on for one minute to 24 hours after which it may be wiped or rinsed off with water, usually during the regular course of personal washing. The composition may also be formulated into a product which is applied to a human body for improving the appearance, cleansing, odor control or general aesthetics.

The composition of the present invention can be in the form of a liquid, lotion, cream, gel or stick form and may be delivered through a roll-on device or using an aerosol can which contains a propellant. "Skin" as used herein is meant to include skin on any part of the body (e.g., neck, chest, back, arms, underarms, hands, legs, buttocks and scalp) especially the underarms.

Melting Point

"Melting point" refers to the temperature at which the solid and liquid forms of a pure substance can exist in equilibrium. "Melting point" for the purpose of the present invention is specified at a standard pressure such as 1 atmosphere.

Oil-In-Water Emulsion

Oil-in-water emulsion comprises an oil phase and a water phase wherein oil phase is the dispersed phase and water is the dispersion medium.

Antiperspirant compositions of the present invention comprise an oil-in-water emulsion.

It is preferred that the droplet size of oil-in-water emulsion of the present invention is 0.02 to 25 microns, and more preferably 0.05 to 10 microns, and furthermore preferably 0.05 to 5 microns. Without wishing to be bound by theory it is believed that the oil-in-water emulsion droplet with smaller sizes are more able to reduce perspiration.

Lipophilic Material

"Lipophilic material" for the purpose of the present invention means a material which tends to combine with or dissolve in lipids, oils or fats.

Without wishing to be bound by theory it is believed that the lipophilic material has to be in solid form upon application of the composition to the skin, e.g., the underarms. Therefore, it is required that the lipophilic material has relatively high melting point.

Antiperspirant composition in accordance with this invention comprises an oil-in-water emulsion comprising an oil phase wherein said oil phase comprises a lipophilic material.

The lipophilic material in accordance with this invention has a melting point greater than 40° C., preferably greater than 45° C., more preferably greater than 48° C.

It is preferred that the lipophilic material is a hydrogenated oil, a fatty alcohol, a fatty acid, a fatty ester, a petroleum oil, a wax or a mixture thereof.

It is more preferred that the lipophilic material is a hydrogenated oil selected from hydrogenated soybean oil, hydrogenated palm oil, hydrogenated corn oil, hydrogenated peanut oil, hydrogenated cottonseed oil, hydrogenated olive oil, hydrogenated avocado oil, hydrogenated castor oil, or a mixture thereof It is more preferred that the lipophilic material is a wax selected from glycerol tristearate, glyceryl tridodecanoat, glycerol cinnamate, carnauba wax, candelilla wax, beeswax, permulgin wax, rice Bran wax, siliconyl candelilla wax, tribehenin, rhuswax, sugarcane wax, C18-36 acid triglyceride, C18-36 acid glycol ester, or a mixture thereof.

It is furthermore preferred that the lipophilic material is selected from hydrogenated soybean oil, hydrogenated palm oil, hydrogenated peanut oil, hydrogenated cottonseed oil, beeswax, tribehenin, or a mixture thereof.

Antiperspirant compositions in accordance with this invention comprises at least 4 wt %, preferably from 4 to 50 wt %, and more preferably from 6 to 40 wt %, and furthermore preferably from 8 to 35 wt % the lipophilic material, based on total weight of the composition.

Without wishing to be bound by theory the inventors believe that once the oil-in-water emulsion droplet is applied, gradual evaporation of the water of emulsion induces the breakdown of the emulsion droplet and the aggregation or coalescence of the lipophilic material which is in solid form thereby form an aggregation/precipitation and which thereby provides antiperspirant benefits.

Antiperspirant compositions in accordance with this invention may advantageously comprise an additional antiperspirant active. However, the composition of the present invention is free from antiperspirant active which comprises aluminium or zirconium. And the composition of the present invention is free from antiperspirant active which is zinc based.

Antiperspirant active which comprises aluminium or zirconium is preferably selected from aluminium/zirconium halides and halohydrate salts, aluminum-zirconium tetrachlorohydrex glycine complex, aluminum-zirconium octachlorohydrex glycine complex, aluminum-zirconium pentachlorohydrate, aluminum sesquichlorohydrate or mixtures thereof, more preferably aluminum sesquichlorohydrate or aluminium chlorohydrates. Antiperspirant active which comprises aluminium or zirconium can also be complexes based on the above-mentioned astringent aluminium and/or zirconium salts and the complex often employs a compound with a carboxylate group, and advantageously this is an amino acid.

Zinc based antiperspirant active is preferably selected from zinc oxide, zinc hydroxide, zinc hydroxide ions with counter ions, and zinc ions with counter ions. Counter ions may include halides and amino acid salt.

Non-aluminum and non-zirconium, non-zinc antiperspirant actives may be present to augment or supplement the antiperspirant activity of the non-thermoplastic polymeric material as disclosed. Non-aluminum or zirconium, or non-zinc antiperspirant active is preferably selected from glycerol monolaurate plus isostearyl alcohol, chitosan or a salt thereof with a weight average molecular weight of from 250 to 650 kDa, titanium compound chelated by alkanolamine with an acid and a polyhydric alcohol, or cholic acid derivative selected from a hydroxycholic acid or a salt thereof with a multivalent metal salt.

More preferably, the composition of the present invention is free from metal based antiperspirant active. The metal includes aluminum, zirconium, zinc, titanium, copper, gallium, stannum, Indium, hafnium, vanadium, cobalt.

Emulsifier

Without wishing to be bound by theory it is believed that the emulsifier acts as an aid to stabilize the lipophilic material in the oil-in-water emulsion droplet in the composition.

Therefore, it is essential to include an emulsifier in the compositions of the present invention.

It is preferred that the emulsifier in accordance with this invention comprises a nonionic emulsifier. It is particularly preferred that the nonionic emulsifier has an HLB value of 10 or lower, more preferably 9 or lower. It is further preferred that the melting point of such nonionic emulsifier is greater than 37° C. It is furthermore preferred that the melting point of such non-ionic emulsifier is greater than 40° C.

It is preferred that the emulsifier is a nonionic emulsifier selected from steareth-2, ceteth-2, polyglyceryl-2 stearate, polyglyceryl-2-distearate, polyglyceryl-3 distearate, sorbitan palmitate, glycerol stearate, glycol stearate, sucrose polystearate, cetyl palmitate, sorbitan tristearate, sorbitan monopalmitate, diethylene glycol monostearate, glycerol monostearate, sorbitan monostearate, PEG-8 beeswax, Sorbeth-20 beeswax, PEG-2 stearate, glyceryl myristate, glyceryl oleate, glyceryl stearate.

It is preferred that the antiperspirant composition in accordance with this invention further comprises a more hydrophilic emulsifier, which is selected from an anionic emulsifier, a cationic emulsifier, an amphoteric emulsifier, a nonionic emulsifier having an HLB of 11 or more.

It is preferred that such more hydrophilic emulsifier is a nonionic emulsifier selected from steareth-20, steareth-21, ceteareth-20, Tween 80, ceteth-20, PEG-40 stearate, PEG-80 sorbitan laurate, Isoceteth-20, Isosteareth-20, laureth-23, Oleth-10, Oleth-20, PEG-100 stearate, PEG-20 methyl glucose sesquistearate, PEG-60 almond glycerides, PEG-8 laurate, polysorbate 20, polysorbate 60, polysorbate 80, polyglyceryl-10 stearate, polyglyceryl-10 monopalmitate.

It is preferred that such more hydrophilic emulsifier is an anionic emulsifier selected from sodium lauryl sulfate and sodium stearoyl glutamate, sodium cocoyl glycinate, sodium methyl cocoyl taurate, sodium cocoyl glutamate, sodium cocoyl isethionate, sodium laureth-13 carboxylate, trideceth-7 carboxylic acid, sodium stearyl glutamate.

It is preferred that such more hydrophilic emulsifier is an amphoteric emulsifier selected from cocamidopropyl betaine, lauryl betaine, betaine citrate, sodium lauroamphoacetate, sodium hydroxymethylglycinate, (carboxymethyl) dimethyloleylammonium hydroxide, (carboxylatomethyl)dimethyl(octadecyl) ammonium.

It is preferred that such more hydrophilic emulsifier is a cationic emulsifier selected from stearamidopropyl dimethylamine, tetramethylammonium acetate, tetra butylammonium hydrogen sulfate, dodecyltrimethylammonium chloride, tetraethylammonium bromide, tetrabutyl ammonium chloride, dimethyldioctadecylammonium bromide.

It is preferred that the antiperspirant composition in accordance with this invention comprises from 0.5 to 40 wt %, and more preferably from 2 to 30 wt %, and furthermore preferably from 4 to 20 wt % the emulsifier, and most preferably from 5 to 20 wt %, based on total weight of the composition.

pH of Compositions

It is preferred that pH of the antiperspirant composition of the present invention is preferably from 2 to 9, more preferably 3 to 7.

Other Ingredients

Other components commonly included in conventional antiperspirant compositions may also be incorporated in the compositions of the present invention. Such components include skin care agents such as emollients, humectants and skin barrier promoters; skin appearance modifiers such as skin lightening agents and skin smoothing agents; anti-microbial agents, in particular organic anti-microbial agents, and preservatives.

The antiperspirant compositions of the invention are applied cosmetically and topically to the skin, broadly speaking, by one of two methods. Different consumers prefer one method or the other. In one method, sometimes called a contact method, the composition is wiped across the surface of the skin, depositing a fraction of the composition as it passes. In the second method, sometimes called the non-contact method, the composition is sprayed from a dispenser held proximate to the skin, often in an area of about 10 to 20 $cm^2$. The spray can be developed by mechanical means of generating pressure on the contents of a dispenser, such as a pump or a squeezable sidewall or by internally generated pressure arising from a fraction of a liquefied propellant volatilizing, the dispenser commonly being called an aerosol.

There are broadly speaking two classes of contact compositions, one of which is liquid and usually applied using a roll-on dispenser or possibly absorbed into or onto a wipe, and in the second of which the antiperspirant active is distributed within a carrier liquid that forms a continuous phase that has been gelled. In one variation, the carrier fluid comprises a solvent for the antiperspirant and in a second variation, the antiperspirant remains a particulate solid that is suspended in an oil, usually a blend of oils.

The composition of the invention comprises an aqueous cosmetically acceptable carrier. The term aqueous means that the composition of the invention comprises water as the main carrier or that water forms a major part of the carrier. In such cases, other solvents and ingredients other than water may also be present.

It is preferred that the composition of the invention is in the form of a cream, a spray, a firm solid, a soft solid or is an emulsion packaged in a roll-on applicator.

It is preferred that, when said composition is a spray it comprises a propellant and the composition is in the form of an aerosol.

Further preferably, the composition of the invention is in the form of a roll-on product.

Roll-On

Alternatively, the composition of the invention is a liquid composition, that can be dispensed from a roll-on package. Antiperspirant roll-on emulsions commonly comprise one or more emulsifiers to maintain a distribution of the water-soluble ingredients.

Aerosol Compositions

Further alternatively, the antiperspirant composition of the invention is delivered through an aerosol composition which comprises a propellant in addition to the applicable other ingredients described hereinabove. Commonly, the propellant is employed in a weight ratio to the base formulation of from 95:5 to 5:95. Depending on the propellant, in such aerosol compositions the ratio of propellant to base formulation is normally at least 20:80, generally at least 30:70, particularly at least 40:60, and in many formulations, the weight ratio is from 90:10 to 50:50. A ratio range of from 70:30 to 90:10 is sometimes preferred.

Propellants herein generally are one of three classes; (i) low boiling-point gasses liquified by compression, (ii) volatile ethers and (iii) compressed non-oxidising gases.

Class (i) is conveniently a low boiling-point material, typically boiling below −5° C., and often below −15° C., and in particular, alkanes and/or halogenated hydrocarbons. This class of propellant is usually liquefied at the pressure in the aerosol canister and evaporates to generate the pressure to expel the composition out of the canister. Examples of suitable alkanes include particularly propane, butane or isobutane. The class (ii) of propellant comprises a very volatile ether of which the most widely employed ether hitherto is dimethyl ether. This propellant can advantageously be employed at relatively low weight ratio of propellant to base formulation, for example to as low as 5:95. It can also be employed in admixture with, for example, compressible/liquefiable alkane gasses. The class (iii) of propellant comprises compressed non-oxidising gasses, and in particular carbon dioxide or nitrogen. Inert gases like neon are a theoretical alternative.

The composition of the present invention can comprise a wide range of other optional components. The CTFA Personal Care Ingredient Handbook, Second Edition, 1992, which is incorporated by reference herein in its entirety, describes a wide variety of non-limiting personal care and pharmaceutical ingredients commonly used in the skin care industry, which are suitable for use in the compositions of the present invention. Examples include: antioxidants, binders, biological additives, buffering agents, colorants, thickeners, polymers, astringents, fragrance, conditioners, exfoliating agents, pH adjusters, other than the ones already discussed earlier, preservatives, natural extracts, essential oils, skin sensates, skin soothing agents, and skin healing agents.

A preservative is a preferred additional component in compositions of the invention. A preservative serves to reduce or eliminate microbial contamination of compositions of the invention. Preservatives are typically employed at a total level of from 0.05 to 3%, preferably at from 0.1 to 2% and most preferably at from 0.4 to 1%.

Suitable preservatives for use with the present invention include 2-phenoxyethanol, polylysine, iodopropynyl butylcarbamate, $C_1$-$C_3$ alkyl parabens, sodium benzoate, caprylyl glycol and EDTA. Particularly preferred preservatives are 2-phenoxyethanol, iodopropynyl butylcarbamate, sodium benzoate, caprylyl glycol and EDTA and especially preferred are 2-phenoxyethanol and iodopropynyl butylcarbamate.

A preferred additional component of compositions of the invention is a fragrance. Suitable materials include conventional perfumes, such as perfume oils and also include so-called deo-perfumes, as described in EP 545,556 and other publications. Levels of incorporation are preferably up to 4% by weight, particularly from 0.1% to 2% by weight, and especially from 0.7% to 1.7% by weight.

An antimicrobial deodorant active is a preferred an additional component in compositions of the invention. Such components serve to reduce or eliminate body odour by reducing or otherwise impeding the function of microbes on the skin of the body responsible for malodour generation.

The antimicrobial deodorant active may also be a preservative for the composition.

When employed, the anti-microbial deodorant agent is typically incorporated into the composition at from 0.01% to 3% and particularly at from 0.03% to 0.5%.

Preferred anti-microbial deodorant agents have a minimum inhibitory concentration (MIC) of 1 $mg \cdot ml^{-1}$ or less, particularly 200 $\mu g \cdot ml^{-1}$ or less, and especially 100 $\mu g \cdot ml^{-1}$ or less. The MIC of an anti-microbial agent is the minimum concentration of the agent required to significantly inhibit microbial growth. Inhibition is considered "significant" if an 80% or greater reduction in the growth of an inoculum of *Staphylococcus epidermidis* is observed, relative to a control medium without an anti-microbial agent, over a period of 16 to 24 hours at 37° C. Details of suitable methods for determining MICs can be found in "Antimicrobial Agents and Susceptibility Testing", C. Thornsberry, (in "Manual of Clinical Microbiology", $5^{th}$ Edition, Ed. A. Balows et al, American Society for Microbiology, Washington D.C., 1991). A particularly suitable method is the Macrobroth Dilution Method as described in Chapter 110 of above publication (pp. 1101-1111) by D. F. Sahm and J. A. Washington II. MICs of anti-microbials suitable for inclusion in the compositions of the invention are triclosan: 0.01-10 $\mu g \cdot ml^{-1}$ (J. Regos et al., Dermatologica (1979), 158: 72-79) and farnesol: ca. 25 $\mu g \cdot ml^{-1}$ (K. Sawano, T. Sato, and R. Hattori, Proceedings of the $17^{th}$ IFSCC International Conference, Yokahama (1992) p. 210-232). By contrast ethanol and similar alkanols have MICs of greater than 1 $mg \cdot ml^{-1}$.

Suitable organic anti-microbials are bactericides, for example quaternary ammonium compounds, like cetyltrimethylammonium salts; chlorhexidine and salts thereof; and diglycerol monocaprate, diglycerol monolaurate, glycerol monolaurate, and similar materials, as described in "Deodorant Ingredients", S. A. Makin and M. R. Lowry, in "Antiperspirants and Deodorants", Ed. K. Laden (1999, Marcel Dekker, New York). More preferred anti-microbials for use in the compositions of the invention are polyhexamethylene biguanide salts (also known as polyaminopropyl biguanide salts), an example being Cosmocil CQ™ available from Zeneca PLC, preferably used at up to 1% and more preferably at 0.03% to 0.3% by weight; 2',4,4'-trichloro,2-hydroxy-diphenyl ether (triclosan), preferably used at up to 1% by weight of the composition and more preferably at 0.05-0.3%; and 3,7,11-trimethyldodeca-2,6,10-trienol (farnesol), preferably used at up to 1% by weight of the composition and more preferably at up to 0.5%.

Other suitable organic antimicrobial agents are transition metal chelators, as described in WO01/52805, for example. Transitional metal chelators having a binding coefficient for iron(III) of greater than $10^{26}$, for example diethylenetriaminepentaacetic acid and salts thereof are preferred.

Method and Use

The present invention also provides for a method of reducing perspiration comprising a step of topical application of the composition of the first aspect. Preferably, the present invention provides for a method wherein the composition of the first aspect is applied on the underarms. The present invention also provides for a method wherein topical application of the composition of the first aspect reduces perspiration from the surface of the human body. The method in accordance with the invention is preferably non-therapeutic. By non-therapeutic is meant that the method is cosmetic in nature.

The invention also provides for use of the composition of the first aspect for reduction of bodily perspiration. The use in accordance with the invention is preferably non-therapeutic in nature, more preferably cosmetic in nature.

The invention provides for use of oil-in-water emulsion comprising a lipophilic material having a melting point greater than 40° C. as an antiperspirant agent.

The invention will now be demonstrated with the help of the following non-limiting examples.

EXAMPLES

Materials listed in Table-1 were put through some tests as detailed hereinafter.

TABLE 1

| Trade name | Chemical ingredient | Supplier | Melting point (° C.) |
|---|---|---|---|
| Refined High Oleic Sunflower Seed Oil | Sunflower seed oil | Kerry KSFL | −5 |
| Casid ® HSA | 12-hydroxystearic acid | Vertellus | 74-76 |
| Hydrogenated Soybean Oil | Hydrogenated Soybean Oil | Wilmar | 52 |

Examples

In the following examples all percentages are by weight, unless otherwise indicated.

The compositions indicated in Table-2 were prepared.

TABLE 2

| Reference No. | Lipophilic material | Emulsifier | Water |
|---|---|---|---|
| A | 4%_Sunflower seed oil | 0.6%_steareth-20_ + 2.6% steareth-2 | To 100% |
| 1 | 4% 12-hydroxystearic acid | 0.6%_steareth-20_ + 2.6% steareth-2 | To 100% |
| 2 | 8% Hydrogenated Soybean Oil | 1.2%_steareth-20_ + 5.2% steareth-2 | To 100% |
| 3 | 12% Hydrogenated Soybean Oil | 0.6% Eumulgin ® SG + 4.5% Emulgade ® Sucro | To 100% |

A composition comprising 12-hydroxystearic acid and sunflower seed oil as given in Table-3 was prepared by a process according to the description set forth in Example 3 of EP Patent No. 2604248 B1.

TABLE 3

| Reference No. | Lipophilic material | Emulsifier | Humectant | Water |
|---|---|---|---|---|
| B | 2% 12-hydroxystearic acid + 4% sunflower seed oil | 0.9% steareth-20 + 2.3% steareth-2 | 4% glycerol | To 100% |

Pore Blocking Rig Measurement

The pore blocking effect of the compositions was measured by a pore blocking rig, according to the procedure described as below:

AE100 membrane filter was treated by evenly spreading 300 mg compositions on surface and followed by heating for 30 minutes at 37° C. with 43% humidity. The pore blocking effect was measured by measuring the flow rate (g/s) of 250 g water passing through the treated membrane filter under 200 mbar pressure. The lower the flow rate is, the pore is better blocked.

Results are summarised in Table-4.

TABLE 4

| Reference No. | Flow rate (g/s) |
|---|---|
| A | 39.68 |
| B | 24.27 |
| 1 | 1.29 |
| 2 | 0.12 |
| 3 | 0.01 |

The results (shown in the Table-4) demonstrate that compositions as per the invention (Reference No. 1 to 3) are capable of forming an aggregation/precipitation under the test conditions disclosed earlier, which further indicates their ability to reduce perspiration when used in an antiperspirant composition, while compositions outside the invention (Examples A to B) do not exhibit such good efficacy.

Hot Room Study

The roll-on composition as per the invention (Reference No. 4) indicated in Table-5 was prepared.

| Trade name | INCI name | Supplier | Level % w/w |
|---|---|---|---|
| Hydrogenated Soybean Oil | Hydrogenated Soybean oil | Wilmar | 12.00 |
| Eumulgin ® SG | Sodium Stearoyl Glutamate | BASF | 0.60 |
| Emulgade ® Sucro | Sucrose Polystearate (and) Hydrogenated Polyisobutene | BASF | 4.50 |
| Pemulen ™ EZ-4U | Acrylates/C10-30 Alkyl Acrylate Crosspolymer | Lubrizol | 0.05 |
| Preservative | — | — | 0.5 |
| Demin Water | Aqua | Lab Supply B406 | 82.30 |

The control sample aerosol formulation (non-antiperspirant) indicated in Table-6 was prepared.

TABLE 6

| Trade Name | INCI | % w/w |
|---|---|---|
| AP40 | Butane/Isobutane/Propane | 55.00 |
| Denatured Ethanol | Alcohol Denat. | 43.50 |
| Fragrance (various) | Parfum | 01.50 |

"Sweat weight reduction" SWR results were obtained on use of each of the compositions using a test panel of 30 female volunteers. Test operators applied test sample Example 4 (0.30 g) to one axilla and 0.30 g of control sample to the other axilla of each panellist. This was done once each day for three days. After the third application, panellists were requested not to wash under their arms for the following 24 hours.

24 hours after the third and final product application, the panellists were induced to sweat in a hot-room at 40° C. (±2° C.) and 40% (±5%) relative humidity, for 40 minutes. After this period, the panellists left the hot-room and their axillae were carefully wiped dry. Pre-weighed cotton pads were then applied to each axilla of each panellist and the panellists re-entered the hot-room for a further 20 minutes. Following this period, the pads were removed and re-weighed, enabling the weight of sweat generated to be calculated.

The sweat weight reduction (SWR) for each panellist was calculated as a percentage (% SWR) and the mean % SWR was calculated according to the method described by Murphy and Levine in "Analysis of Antiperspirant Efficacy Results", *J. Soc. Cosmetic Chemists,* 1991(May), 42, 167-197.

The result showed that the Example 4 gave a SWR of 14%, illustrating the perspiration reduction benefit.

The invention claimed is:

1. A composition free from aluminum and/or zirconium salt, and/or zinc based antiperspirant active, the composition comprising an oil-in-water emulsion, wherein the oil-in-water emulsion comprises an oil phase comprising a lipophilic material having a melting point greater than 48° C. and which is a hydrogenated oil;

wherein the oil-in-water emulsion comprises a nonionic emulsifier having an HLB value of 9 or lower and a melting point of greater than 40° C.;

wherein the composition comprises 8 to 35% of the lipophilic material based on total weight of the composition;

wherein the hydrogenated oil comprises hydrogenated soybean oil;

wherein the oil-in-water emulsion has a droplet size ranging from 5 to 25 microns;

wherein the composition comprises 5 to 20 wt % of the nonionic emulsifier based on total weight of the composition;

and further wherein the composition is a liquid composition that can be dispensed from a roll-on package.

2. The composition as claimed in claim 1, wherein the nonionic emulsifier is at least one of steareth-2, ceteth-2, polyglyceryl-2 stearate, polyglyceryl-2-distearate, polyglyceryl-3 distearate, sorbitan palmitate, glycerol stearate, glycol stearate, sucrose polystearate, cetyl palmitate, sorbitan tristearate, sorbitan monopalmitate, diethylene glycol monostearate, glycerol monostearate, sorbitan monostearate, PEG-8 beeswax, PEG-2 stearate, glyceryl myristate, glyceryl oleate, and glyceryl stearate.

3. The composition as claimed in claim 1, wherein the composition comprises a fragrance.

4. The composition as claimed in claim 1, wherein the composition comprises an antimicrobial deodorant.

5. The composition as claimed in claim 1, wherein the composition comprises a preservative.

6. A method of reducing perspiration comprising a step of topical application of the composition as claimed in claim 1.

* * * * *